US00PP22262P2

(12) United States Plant Patent
Nijssen

(10) Patent No.: US PP22,262 P2
(45) Date of Patent: Nov. 22, 2011

(54) ***ACHILLEA* PLANT NAMED 'PEACHY SEDUCTION'**

(50) Latin Name: *Achillea millefolium*
Varietal Denomination: Peachy Seduction

(75) Inventor: Wilhelmus J. J. Nijssen, Den Haag (NL)

(73) Assignee: K. Sahin Zaden B.V., De Kwakel (NL)

( * ) Notice: Subject to any disclaimer, the term of this patent is extended or adjusted under 35 U.S.C. 154(b) by 0 days.

(21) Appl. No.: 12/804,003

(22) Filed: Jul. 12, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Achillea* plant named 'Peachy Seduction', characterized by its upright, columnar and mounded plant habit; strong and vigorous growth habit; freely branching habit; freely flowering habit with plants remaining in flower for a long period time; inflorescences with peachy pink-colored ray florets; and good garden performance.

1 Drawing Sheet

Botanical designation: *Achillea millefolium.*
Cultivar denomination: 'PEACHY SEDUCTION'.

CROSS-REFERENCED TO RELATED APPLICATION

Title: *Achillea* Plant Named 'Pineapple Mango'
Applicant: Wilhelmus J. J. Nijssen
Filed: Concurrently with this application

BACKGROUND OF THE INVENTION

The present invention relates to a new and distinct cultivar of *Achillea* plant, botanically known as *Achillea millefolium,* and hereinafter referred to by the name 'Peachy Seduction'.

The new *Achillea* plant is a naturally-occurring whole plant mutation of *Achillea millefolium* 'Summer Pastels', not patented. The new *Achillea* plant was discovered and selected by the Inventor as a single flowering plant within a population of plants of 'Summer Pastels' in July, 2005 in a controlled outdoor nursery environment in Stavenisse, The Netherlands. The selection of this plant was based on its unique inflorescence coloration.

Asexual reproduction of the new *Achillea* plant by vegetative cuttings in a controlled environment in Lancaster, Pa. since August, 2006, has shown that the unique features of this new *Achillea* plant are stable and reproduced true to type in successive generations.

SUMMARY OF THE INVENTION

Plants of the new *Achillea* have not been observed under all possible environmental conditions. The phenotype may vary somewhat with variations in environment such as temperature and light intensity, without, however, any variance in genotype.

The following traits have been repeatedly observed and are determined to be the unique characteristics of 'Peachy Seduction'. These characteristics in combination distinguish 'Peachy Seduction' as a new and distinct cultivar of *Achillea* plant:

1. Upright, columnar and mounding plant habit.
2. Strong and vigorous growth habit.
3. Freely branching habit.
4. Freely flowering habit with plants remaining in flower for a long period time.
5. Inflorescences with peachy pink-colored ray florets.
6. Good garden performance.

Plants of the new *Achillea* differ from plants of the parent, 'Summer Pastels', in the following characteristics:

1. Plants of the new *Achillea* are more compact than and not as open as plants of 'Summer Pastels'.
2. Plants of the new *Achillea* are more freely branching and have stronger stems than plants of 'Summer Pastels'.
3. Plants of the new *Achillea* flower more uniformly than plants of 'Summer Pastels'.
4. Ray florets of plants of the new *Achillea* are peachy pink in color whereas ray florets of 'Summer Pastels' are medium pink in color; additionally, ray floret color of plants of the new *Achillea* does not fade as quickly as ray floret color of plants of 'Summer Pastels'.

Plants of the new *Achillea* differ primarily in ray floret coloration from plants of *Achillea millefolium* 'Pineapple Mango', disclosed in a U.S. Plant patent application Ser. No. 12/804,004 filed concurrently.

Plants of the new *Achillea* can also be compared to plants of *Achillea millefolium* 'Paprika', not patented. In side-by-side comparisons conducted in Lancaster, Pa., plants of the new *Achillea* differed from plants of 'Paprika' in the following characteristics:

1. Plants of the new *Achillea* were more freely branching than plants of 'Paprika'.
2. Plants of the new *Achillea* had shorter internodes than plants of 'Paprika'.
3. Ray floret color of plants of the new *Achillea* did not fade as quickly as ray floret color of plants of 'Paprika'.

BRIEF DESCRIPTION OF THE PHOTOGRAPHS

The accompanying photographs illustrate the overall appearance of the new *Achillea* plant. These photographs show the colors as true as it is reasonably possible to obtain in colored reproductions of this type. Colors in the photographs may differ slightly from the color values cited in the detailed botanical description which accurately describe the colors of the new *Achillea* plant.

The photograph at the bottom of the sheet comprises a side perspective view of a typical flowering plant of 'Peachy Seduction' grown in a container.

The photograph at the top of the sheet is a close-up view of typical inflorescences of 'Peachy Seduction'.

DETAILED BOTANICAL DESCRIPTION

Plants used for the aforementioned photographs and following observations and measurements describe plants grown in 20-cm containers in an outdoor nursery in Lancaster, Pa. during the spring and summer and under conditions and practices which approximate those generally used in commercial *Achillea* production. During the production of the plants, day temperatures ranged from 18° C. to 29° C. and night temperatures ranged from 13° C. to 21° C. Plants were pinched one time about 12 weeks after planting. Measurements and numerical values represent averages for typical nine-month old flowering plants. In the following description, color references are made to The Royal Horticultural Society Colour Chart, 2007 Edition, except where general terms of ordinary dictionary significance are used.

Botanical classification: *Achillea millefolium* 'Peachy Seduction'.

Parentage: Naturally-occurring whole plant mutation *Achillea millefolium* 'Summer Pastels', not patented.

Propagation:

*Type.*—Terminal vegetative cuttings.

*Time to initiate roots, summer.*—About five days at 22° C.

*Time to initiate roots, winter.*—About seven days at 20° C.

*Time to produce a rooted cutting, summer.*—About 21 days at 24° C.

*Time to produce a rooted cutting, winter.*—About 25 days at 22° C.

*Root description.*—Thick, fleshy; white in color.

*Rooting habit.*—Freely branching; moderately dense.

Plant description:

*Plant form/growth habit.*—Upright, columnar and mounding plant habit; strong and sturdy plants; vigorous growth habit.

*Plant height.*—About 44 cm.

*Plant diameter or spread.*—About 47 cm.

*Lateral branches.*—Quantity per plant: Freely branching habit with about 20 lateral branches developing per plant; pinching enhances lateral branch development. Length: About 45 cm. Diameter: About 5 mm. Internode length: About 3.5 cm. Aspect: Mostly upright. Strength: Strong, sturdy. Texture: Tomentose. Color: Close to 146C.

Foliage description:

*Arrangement.*—Alternate, simple; sessile.

*Length.*—About 10.5 cm.

*Width.*—About 2 cm.

*Shape.*—Lanceolate; pinnatifid.

*Apex.*—Acute.

*Base.*—Truncate.

*Margin.*—Very finely dissected giving a fern-like feathery appearance.

*Texture, upper and lower surfaces.*—Pubescent.

*Venation pattern.*—Pinnate.

*Color.*—Developing leaves, upper surface: Close to 144A. Developing leaves, lower surface: Close to 144B. Fully expanded leaves, upper surface: Close to 147A; venation, close to 147C. Fully expanded leaves, lower surface: Close to 147B; venation, close to 147C.

Inflorescence description:

*Flowering arrangement and habit.*—Rotate composite inflorescence form; inflorescences arranged in terminal or axillary compound cymes; cymes somewhat flat-topped; freely flowering habit with about 900 inflorescences developing per lateral branch; inflorescences positioned above the foliar plane and face upright to slightly outwardly.

*Fragrance.*—Moderate; grassy.

*Time to flower.*—Long flowering period, under natural season conditions, plants flower throughout the summer; plants that are cut back will reflower.

*Post-production longevity.*—Inflorescences maintain good substance for about five to seven days on the plant; inflorescences persistent.

*Inflorescence bud.*—Height: About 5 mm. Diameter: About 2.5 mm. Shape: Ovoid. Color: Close to 37C.

*Cyme size.*—Diameter: About 6 cm by 7 cm. Height: About 6.5 cm.

*Inflorescence size.*—Diameter: About 1 cm. Depth (height): About 8 mm. Disc diameter: About 3 mm. Receptacle diameter: About 3 mm. Receptacle height: About 4 mm. Receptacle shape: Ovoid. Receptacle color: Close to 146C.

*Ray florets.*—Shape: Rounded obovate. Apex: Emarginate. Base: Attenuate. Margin: Entire. Length: About 4 mm. Width: About 4 mm. Texture, upper and lower surfaces: Smooth, glabrous. Number of ray florets per inflorescence: Five in a single whorl. Color: When opening and fully opened, upper surface: Close to 37B to 37C; color becoming closer to 29C with development. When opening and fully opened, lower surface: Close to 38D; color becoming closer to 29D with development.

*Disc florets.*—Arrangement: Massed in the center of the receptacle. Shape: Tubular; apex, five-pointed. Length: About 5 mm. Diameter: About 1 mm. Number of disc florets per inflorescence: About 24. Color, immature: Apex and mid-section: Close to 4C. Base: Close to 145D. Color, mature: Apex and mid-section: Close to 18B. Base: Close to 145D.

*Phyllaries.*—Quantity per inflorescence: About 24 in about four whorls; imbricate. Shape: Lanceolate to narrowly elliptical. Apex: Acute. Base: Truncate. Margin: Entire. Length: About 3 mm. Width: About 1.5 mm. Texture, upper surface: Smooth; glabrous. Texture, lower surface: Pubescent. Color, upper surface: Close to 145B. Color, lower surface: Close to 146C to 146D.

*Peduncles.*—Length, terminal peduncle: About 1 cm. Length, fourth peduncle: About 4 cm. Length, seventh peduncle: About 11.7 cm. Diameter: About 2 mm. Strength: Strong. Aspect: Mostly upright; axillary peduncles, about 45° from vertical. Texture: Pubescent. Color: Close to 148B.

*Reproductive organs* (*present on disc florets only*).—Androecium: Quantity of stamens per disc floret: About five. Filament length: About 2 mm. Filament color: Close to 157D. Anther shape: Rounded. Anther length: Less than 1 mm. Anther color: Close to 7D. Pollen amount: Scarce. Pollen color: Close to 7C. Gynoecium: Quantity of pistils per disc floret: One. Pistil length: About 4 mm. Stigma shape: Bi-parted. Stigma color: Close to 8D. Style length: About 2.5 mm. Style color: Close to 145D. Ovary color: Close to 157D.

*Seed/fruit.*—Seed and fruit production has not been observed.

Disease/pest resistance: Plants of the new *Achillea* have not been shown to be resistant to pathogens and pests common to *Achillea*.

Garden performance: Plants of the new *Achillea* have been observed to have good garden performance and tolerate wind, rain and to be hardy to USDA Hardiness Zone 5.

It is claimed:

1. A new and distinct *Achillea* plant named 'Peachy Seduction' as illustrated and described.

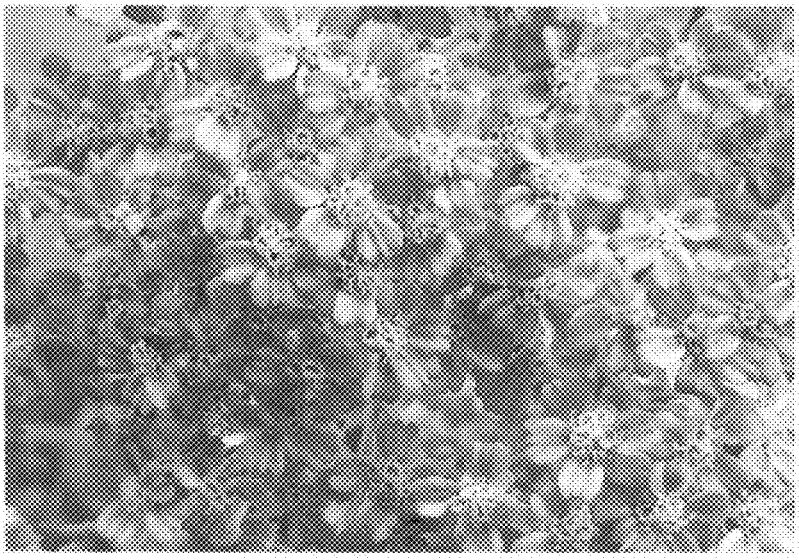
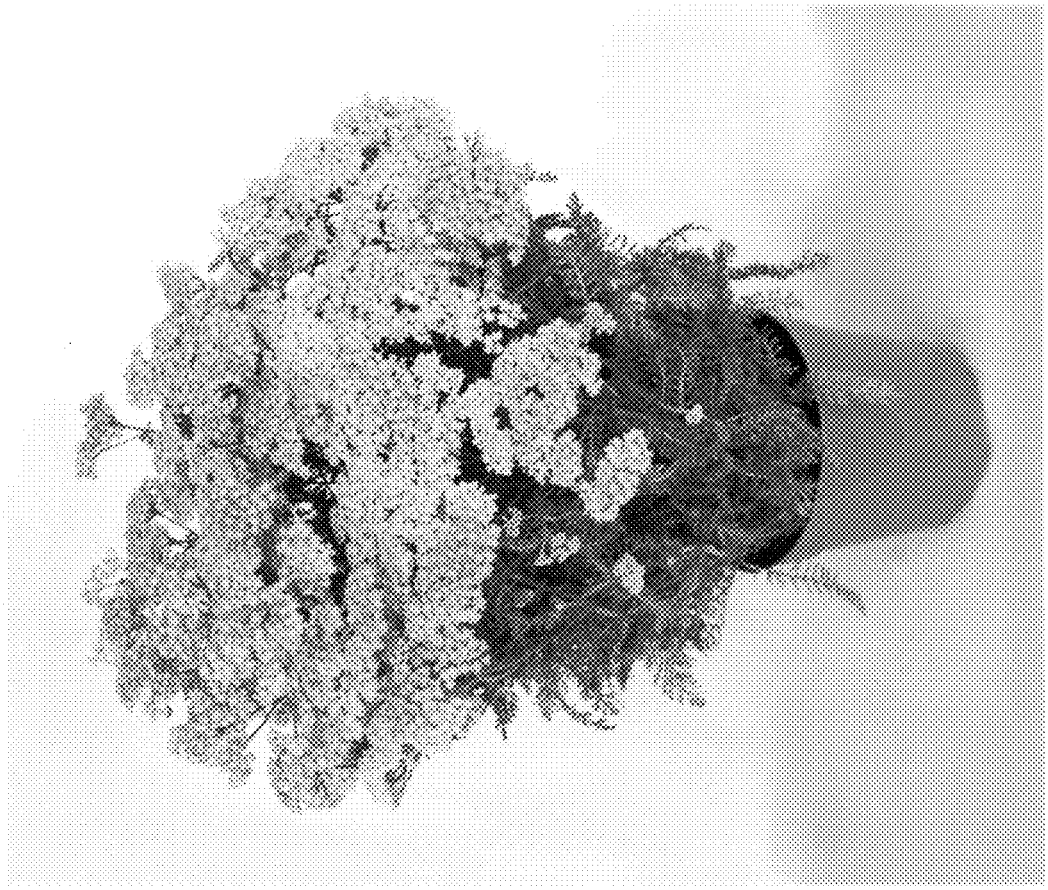

* * * * *